United States Patent
Thornton

(12) 
(10) Patent No.: US 7,932,383 B2
(45) Date of Patent: *Apr. 26, 2011

(54) CRYSTALLINE FORMS OF [(1R), 2S]-2-AMINOPROPIONIC ACID 2-[4-(4-FLUORO-2-METHYL-1H-INDOL-5-YLOXY)-5-METHYLPYRROLO[2,1-F][1,2,4]TRIAZIN-6-YLOXY]-1-METHYLETHYL ESTER

(75) Inventor: John E. Thornton, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/480,177

(22) Filed: Jun. 8, 2009

(65) Prior Publication Data

US 2009/0247531 A1 Oct. 1, 2009

Related U.S. Application Data

(63) Continuation of application No. 11/527,864, filed on Sep. 27, 2006, now abandoned.

(60) Provisional application No. 60/721,021, filed on Sep. 27, 2005.

(51) Int. Cl.
C07D 487/04 (2006.01)
A61K 31/53 (2006.01)
A61P 3/10 (2006.01)

(52) U.S. Cl. ........................ 544/183; 514/243

(58) Field of Classification Search ............ 544/183; 514/243

See application file for complete search history.

(56) References Cited

U.S. PATENT DOCUMENTS 6,869,952 B2 * 3/2005 Bhide et al. .................. 514/243
6,982,265 B1 1/2006 Hunt et al.
7,671,199 B2 * 3/2010 Crispino et al. ............. 544/183

FOREIGN PATENT DOCUMENTS

WO WO 2006/030941 3/2006
WO WO 2006/124689 11/2006

OTHER PUBLICATIONS

Bennett, J.C. et al., eds., Cecil Textbook of Medicine, 20th Edition, vol. 1, W.B. Saunders Company, publ., pp. 1004-1010 (1996).
Fabbro, D. et al., "Protein kinases as targets for anticancer agents: from inhibitors to useful drugs", Pharmacology & Therapeutics, vol. 93, pp. 79-98 (2002).
Gautschi, O. et al., "Aurora Kinases as Anticancer Drug Targets", Clin. Cancer Res., vol. 14, No. 6, pp. 1639-1648 (2008).
Huynh, H. et al., "Brivanib Alaninate, a Dual Inhibitor of Vascular Endothelial Growth Factor Receptor and Fibroblast Growth Factor Receptor Tyrosine Kinases, Induces Growth Inhibition in Mouse Models of Human Hepatocellular Carcinoma", Clin. Cancer Res., vol. 14, No. 19, pp. 6146-6153 (2008).
Mass, R.D., "The HER Receptor Family: a Rich Target for Therapeutic Development", Int, J. Radiation Oncology Biol. Phys., vol. 58, No. 3, pp. 932-940 (2004).
Mountzios, G. et al., "Aurora kinases as targets for cancer therapy", Cancer Treatment Reviews, vol. 34, pp. 175-182 (2008).
National Cancer Institute, www.cancer.gov, Brivanib Active Trial Listing (ID#: 5552473) (Dec. 15, 2008).

* cited by examiner

*Primary Examiner* — Venkataraman Balasubramanian
(74) *Attorney, Agent, or Firm* — Elliott Korsen

(57) ABSTRACT

Crystalline form, Form N-1, of [(1R),2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester (Compound I) is provided. Also provided are a pharmaceutical composition and an oral dosage form comprising the Form N-1 of Compound I as well as a method of using the Form N-1 of Compound I in the treatment of cancer and other proliferative diseases.

6 Claims, 3 Drawing Sheets

CRYSTALLINE FORMS OF [(1R), 2S]-2-AMINOPROPIONIC ACID 2-[4-(4-FLUORO-2-METHYL-1H-INDOL-5-YLOXY)- 5-METHYLPYRROLO[2,1-F][ 1,2,4] TRIAZIN-6- YLOXY]-1-METHYLETHYL ESTER

RELATED APPLICATION

This application is a continuation of U.S. application Ser. No. 11/527,864 filed Sep. 27, 2006 which claims priority benefit under Title 35 §119(e) of U.S. provisional Application No. 60/721,021, filed Sep. 27, 2005, the contents of which are herein incorporated by reference.

FIELD OF THE INVENTION

The present invention generally relates to a crystalline form of [(1R), 2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester. The present invention also relates to a pharmaceutical composition and an oral dosage form comprising the crystalline form of [(1R), 2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester, as well as a method of using the crystalline form of [(1R), 2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester in the treatment of cancer and other proliferative diseases.

BACKGROUND OF THE INVENTION

[(1R), 2S]-2-Aminopropionic acid 2-[4-(4-fluoro-2-methyl-1H-indol-5-yloxy)-5-methylpyrrolo[2,1-f][1,2,4]triazin-6-yloxy]-1-methylethyl ester, has the structure of formula I:

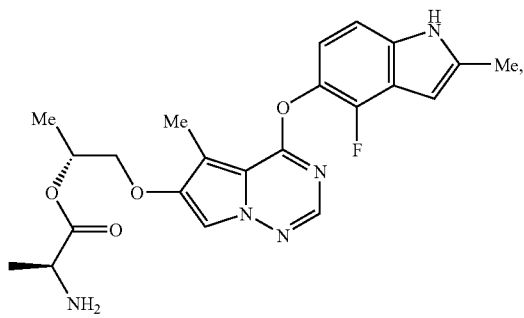

(I)

and is referred to herein as "Compound I". Compound I, compositions comprising Compound I, and methods of using Compound I are disclosed in U.S. Pat. No. 6,869,952 B2, which is assigned to the present assignee and is incorporated herein by reference in its entirety.

Compound I, a prodrug, is suitable for inhibiting tyrosine kinase activity of growth factor receptors such as VEGFR-2 and FGFR-1 and is useful in the treatment of cancer. Compound I is also useful in the treatment of diseases, other than cancer, which are associated with signal transduction pathways operating through growth factors and anti-angiogenesis receptors such as VEGFR-2.

Typically, in the preparation of a pharmaceutical composition, a form of the active ingredient having desired properties such as dissolution rate, solubility, bioavailability, and/or storage stability is sought. For example, a form of the active ingredient, which has the desired solubility and bioavailability, has sufficient stability that it does not convert during manufacture or storage of the pharmaceutical composition to a different form having different solubility and/or bioavailibility. A form of Compound I is desired having properties and stability that allow the preparation of pharmaceutical compositions suitable for the treatment of diseases such as cancer.

SUMMARY OF THE INVENTION

A first aspect of the present invention provides a crystalline form of Compound I:

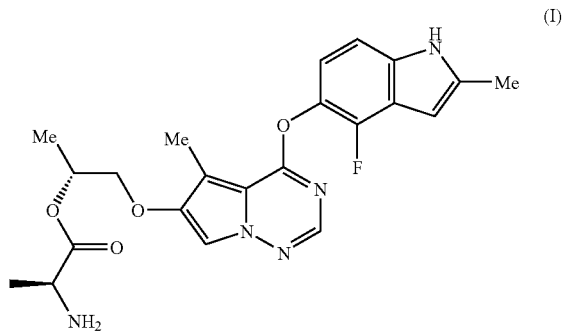

(I)

comprising Form N-1.

A second aspect of the invention provides a pharmaceutical composition comprising the crystalline Form N-1 of Compound I and a pharmaceutically acceptable carrier or diluent.

A third aspect of the present invention provides an oral dosage form comprising Compound I, wherein Compound I is provided in a crystalline form comprising Form N-1.

A fourth aspect of the present invention provides a method for treating a proliferative disease, comprising administering to a mammalian species in need thereof, a therapeutically effect amount of Compound I, wherein Compound I is provided in a crystalline form comprising Form N-1.

The names used herein to characterize a specific form, e.g. "N-1" etc., should not be considered limiting with respect to any other substance possessing similar or identical physical and chemical characteristics, but rather it should be understood that these designations are mere identifiers that should be interpreted according to the characterization information also presented herein.

BRIEF DESCRIPTION OF THE DRAWINGS

The invention is illustrated by reference to the accompanying drawings described below.

DETAILED DESCRIPTION OF THE INVENTION

Figure 1:
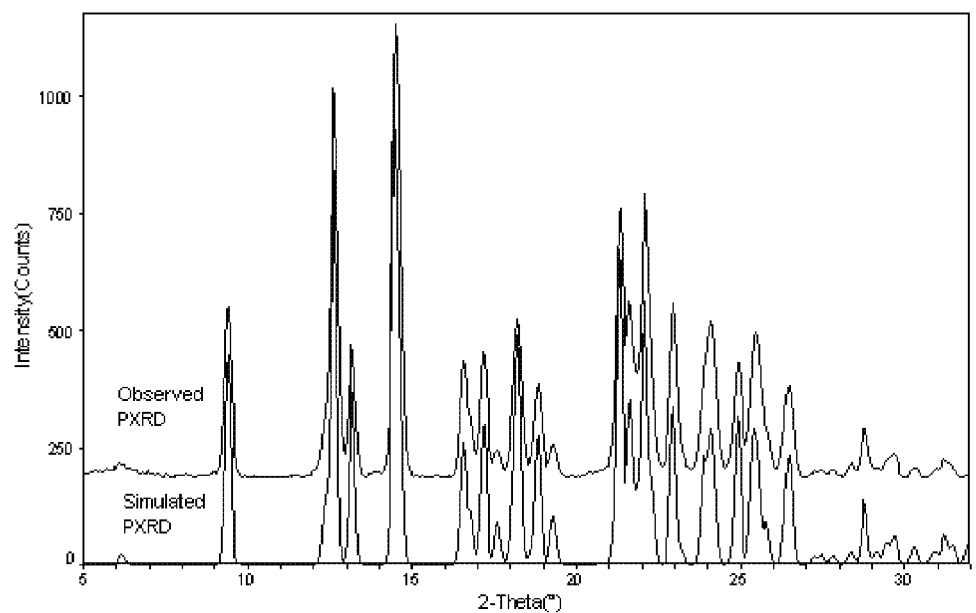
FIG. 1 shows observed and simulated powder x-ray diffraction patterns (CuKαλ=1.5418 Å at T=25° C.) of the N-1 crystalline form of [(1R), 2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester.

As used herein, "polymorphs" refer to crystalline forms having the same chemical compositions but different spatial arrangements of the molecules and/or ions forming the crystals.

As used herein, "amorphous" refers to a solid form of a molecule and/or ions that is not crystalline. An amorphous solid does not display a definitive X-ray diffraction pattern with sharp maxima.

As used herein, "substantially pure", when used in reference to a crystalline form, means a sample of the crystalline form of the compound having a purity greater than 90 weight %, including greater than 90, 91, 92, 93, 94, 95, 96, 97, 98, and 99 weight %, and also including equal to about 100 weight % of the compound, based on the weight of the compound. The remaining material comprises other form(s) of the compound, and/or reaction impurities and/or processing impurities arising from its preparation. For example, a crystalline form of Compound I may be deemed substantially pure in that it has a purity greater than 90 weight % of the crystalline form of Compound I, as measured by means that are at this time known and generally accepted in the art, where the remaining less than 10 weight % of material comprises other form(s) of Compound I and/or reaction impurities and/or processing impurities. The presence of reaction impurities and/or processing impurities may be determined by analytical techniques known in the art, such as, for example, chromatography, nuclear magnetic resonance spectroscopy, mass spectrometry, or infrared spectroscopy.

As used herein, the unit cell parameter "molecules/unit cell" refers to the number of molecules of Compound I in the unit cell.

When dissolved, the crystalline form of Compound I loses its crystalline structure, and is therefore referred to as a solution of Compound I. Crystalline Form N-1 of Compound I may be used for the preparation of liquid formulations in which the compound is dissolved or suspended. In addition, the crystalline Form N-1 of Compound I may be incorporated into solid formulations.

A therapeutically effective amount of the crystalline Form N-1 of Compound I may be combined with a pharmaceutically acceptable carrier or diluent to provide pharmaceutical compositions of this invention. By "therapeutically effective amount", it is meant an amount that, when administered alone or an amount when administered with an additional therapeutic agent, is effective to prevent, suppress, or ameliorate a disease or condition or the progression of a disease or condition.

The present invention provides a crystalline form of Compound I,

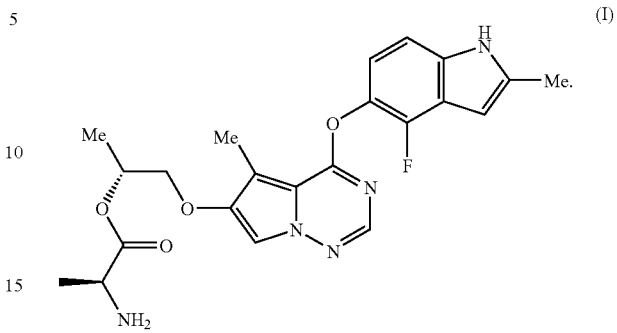

(I)

The crystalline form is a neat crystalline form of Compound I and is referred herein as the "N-1 Form".

In one embodiment, the N-1 Form of Compound I is characterized by unit cell parameters approximately equal to the following:

Cell dimensions: a=9.85 Å
b=8.06 Å
c=14.98 Å
α=90.0°
β=106.9°
γ=90.0°
Space group: P2$_1$,
Molecules/unit cell: 2
Volume=1137.7 Å$^3$
Density (calculated)=1.289 g/cm$^3$
wherein measurement of said crystalline form is at a temperature of about 25° C.

In a different embodiment, the N-1 Form of Compound I is characterized by fractional atomic coordinates substantially as listed in Table 1.

TABLE 1

Positional Parameters and Isotropic Temperature Factors for Form N-1 of Compound I

| Atom | X | Y | V | B(iso) |
| --- | --- | --- | --- | --- |
| N1 | 0.1753(6) | 0.332(6) | 0.1945(4) | 4.5(1) |
| F2 | 0.7015(6) | 0.490(6) | 0.2322(4) | 7.4(1) |
| N3 | 0.4379(7) | 0.291(5) | 0.3144(5) | 5.7(1) |
| C4 | 0.2652(8) | 0.468(6) | 0.2142(5) | 5.1(1) |
| O5 | −0.2575(7) | 0.807(6) | 0.1106(5) | 6.6(1) |
| C6 | 0.3977(8) | 0.436(6) | 0.2779(6) | 4.9(1) |
| C7 | 0.8707(9) | 0.549(6) | 0.3780(6) | 5.4(2) |
| C8 | 0.0601(9) | 0.543(6) | 0.1156(6) | 5.2(2) |
| N9 | 0.2102(8) | 0.175(6) | 0.2301(5) | 6.0(1) |
| O10 | −0.0356(8) | 0.651(6) | 0.0632(5) | 7.1(2) |
| C11 | 0.0471(8) | 0.377(6) | 0.1340(6) | 5.2(1) |
| N12 | 1.0349(8) | 0.609(6) | 0.5111(6) | 6.2(2) |
| C13 | −0.2106(8) | 0.957(5) | 0.1410(5) | 4.8(1) |
| C14 | −0.2689(9) | 0.752(6) | 0.0168(6) | 5.7(2) |
| C15 | 0.896(1) | 0.593(6) | 0.4733(6) | 5.7(2) |
| O16 | 0.4805(8) | 0.571(6) | 0.2994(5) | 7.2(2) |
| C17 | 1.103(1) | 0.582(6) | 0.4457(6) | 5.9(2) |
| C18 | 0.337(1) | 0.170(6) | 0.2876(7) | 6.0(2) |
| C19 | 1.006(1) | 0.548(6) | 0.3630(6) | 5.9(2) |
| C20 | −0.1928(9) | 0.978(6) | 0.2425(6) | 5.4(1) |
| C21 | 0.192(1) | 0.6030(6) | 0.1648(6) | 6.0(2) |
| C22 | 0.7301(9) | 0.530(6) | 0.3229(6) | 5.7(2) |
| O23 | −0.1971(9) | 1.067(6) | 0.0900(6) | 7.9(2) |
| N24 | −0.1133(9) | 1.130(5) | 0.2815(6) | 6.9(2) |
| C25 | 0.622(1) | 0.561(6) | 0.3608(7) | 6.5(2) |
| C26 | 0.647(1) | 0.600(6) | 0.4545(8) | 7.0(2) |

TABLE 1-continued

Positional Parameters and Isotropic Temperature Factors for Form N-1 of Compound I

| Atom | X | Y | V | B(iso) |
|---|---|---|---|---|
| C27 | −0.1781(9) | 0.602(5) | 0.0279(6) | 6.0(2) |
| C28 | 0.781(1) | 0.613(6) | 0.5101(7) | 6.9(2) |
| C29 | −0.332(1) | 0.969(5) | 0.2614(8) | 7.3(2) |
| C30 | 1.261(1) | 0.608(5) | 0.4672(9) | 7.6(2) |
| C31 | −0.426(1) | 0.723(6) | −0.0321(1) | 9.7(3) |
| C32 | 0.246(2) | 0.775(6) | 0.166(1) | 9.1(3) |
| H33 | −0.0444 | 0.2942 | 0.1053 | 5.9159 |
| H34 | 1.0869 | 0.6372 | 0.5838 | 7.2815 |
| H35 | −0.2278 | 0.8448 | −0.0201 | 7.092 |
| H36 | 0.371 | 0.0448 | 0.3177 | 6.7846 |
| H37 | 1.0278 | 0.5242 | 0.2971 | 6.9187 |
| H38 | −0.1326 | 0.8694 | 0.2792 | 6.2069 |
| H39 | 0.564 | 0.6129 | 0.4838 | 8.6991 |
| H40 | −0.2086 | 0.5118 | 0.0747 | 7.0122 |
| H41 | −0.1973 | 0.5371 | −0.0399 | 7.0122 |
| H42 | 0.8024 | 0.6379 | 0.584 | 8.3185 |
| H43 | 1.2929 | 0.5738 | 0.4072 | 9.183 |
| H44 | 1.3124 | 0.5163 | 0.5239 | 9.183 |
| H45 | 1.2882 | 0.7267 | 0.4905 | 9.183 |
| H46 | −0.4376 | 0.6764 | −0.1023 | 11.2165 |
| H47 | −0.4852 | 0.8276 | −0.0316 | 11.2165 |
| H48 | −0.4611 | 0.6193 | 0.0059 | 11.2165 |
| H49 | 0.1629 | 0.8462 | 0.1181 | 12.1131 |
| H50 | 0.3367 | 0.7700 | 0.1367 | 12.1131 |
| H51 | 0.2760 | 0.8228 | 0.2327 | 12.1131 |
| H52 | −0.3172 | 0.9408 | 0.3368 | 8.4573 |
| H53 | −0.3957 | 0.8650 | 0.223 | 8.4573 |
| H54 | −0.396 | 1.0803 | 0.2447 | 8.4573 |
| H55 | −0.1754 | 1.2337 | 0.2473 | 8.0256 |
| H56 | −0.0126 | 1.1268 | 0.2706 | 8.0256 |

In a still different embodiment, the N-1 Form of Compound I is characterized by a powder x-ray diffraction pattern substantially in accordance with that shown in FIG. 1.

Figure 2:
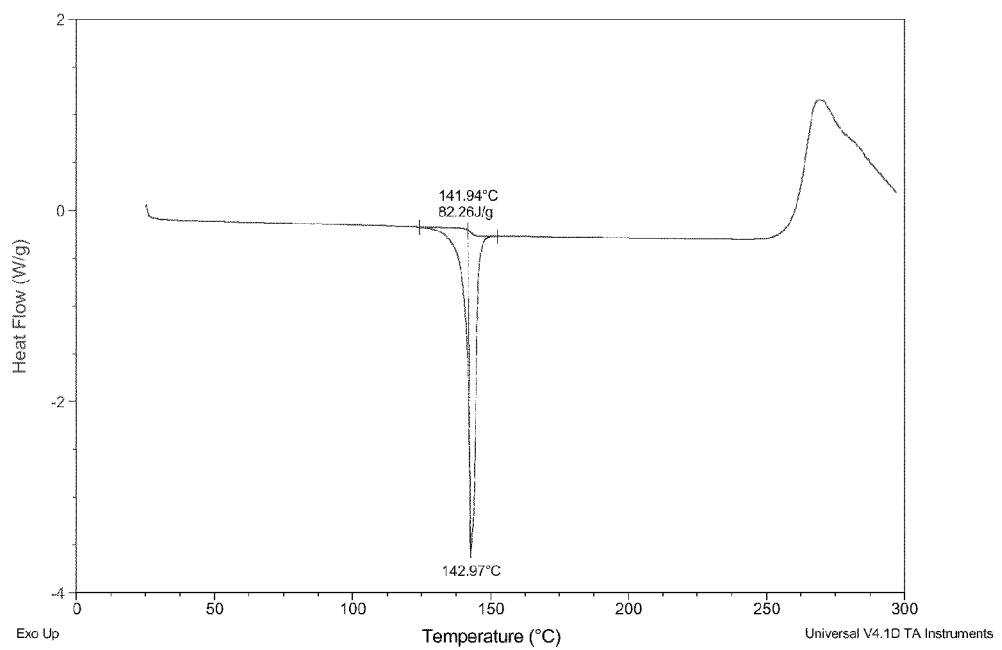
FIG. 2 shows a differential scanning calorimetry thermogram of the N-1 crystalline form of [(1R), 2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester.

In a further embodiment, the N-1 Form of Compound I is characterized by a differential scanning calorimetry thermogram substantially in accordance with that shown in FIG. 2. The N-1 Form may be characterized by a melting point in the range of from about 138° C. to about 144° C.

In a still further embodiment, the N-1 Form of Compound I is characterized by a powder x-ray diffraction pattern (CuKαλ=1.5418 Å at a temperature of about 25° C.) comprising four or more 2θ values, preferably comprising five or more 2θ values, selected from the group consisting of: 9.4±0.2, 12.6±0.2, 13.2±0.2, 14.5±0.2, 16.6±0.2, 17.2±0.2, 18.2±0.2, 18.8±0.2, 21.3±0.2, 21.6±0.2, and 22.1±0.2.

In another embodiment, the N-1 Form is in substantially pure form. This crystalline form of Compound I in substantially pure form may be employed in pharmaceutical compositions which may optionally include one or more other components selected, for example, from excipients and carriers; and optionally, one or more other active pharmaceutical ingredients having active chemical entities of different molecular structures.

Preferably, the N-1 crystalline form has substantially pure phase homogeneity as indicated by less than 10%, preferably less than 5%, and more preferably less than 2% of the total peak area in the experimentally measured powder x-ray diffraction (PXRD) pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

In one embodiment, the N-1 Form is in substantially pure form, wherein substantially pure is greater than 90 weight % pure, preferably greater than 95 weight % pure, and more preferably greater than 99 weight % pure.

In a different embodiment, a composition is provided consisting essentially of the crystalline Form N-1 of Compound I. The composition of this embodiment may comprise at least 90 weight %, preferably at least 95 weight %, and more preferably at least 99 weight % of the crystalline Form N-1 of Compound I, based on the weight of Compound I in the composition.

Figure 3:
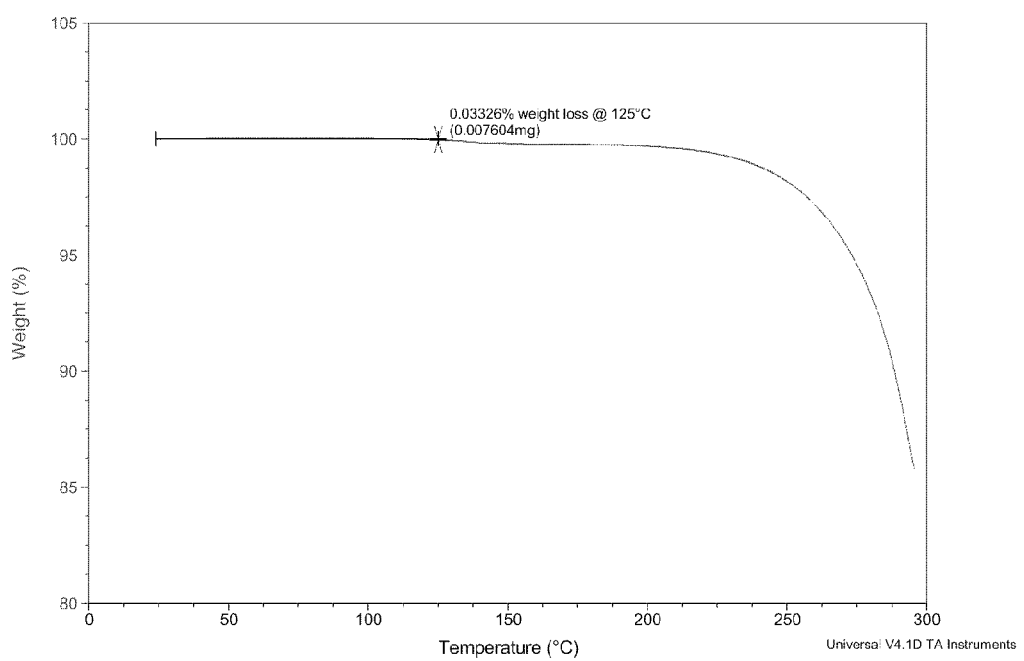
FIG. 3 shows a thermogravimetric analysis (TGA) thermogram of the N-1 crystalline form of [(1R), 2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester.

In yet another embodiment, the N-1 crystalline form of Compound I may be characterized by a thermogravimetric analysis (TGA) thermogram having minimal weight loss in accordance to a neat form. The invention also provides Form N-1 crystal that exhibits a TGA thermogram substantially the same as shown in FIG. 3.

The present invention also provides a pharmaceutical composition comprising a crystalline form of Compound I, wherein Compound I is in Form N-1; and a pharmaceutically acceptable carrier or diluent. The pharmaceutical composition may comprise the Form N-1 in substantially pure form.

In one embodiment, an oral dosage form is provided comprising Compound I wherein Compound I is in a crystalline form comprising Form N-1. The oral dosage form may comprise Compound I wherein Compound I consists essentially of Form N-1. Alternatively, the oral dosage form may comprise Compound I wherein Compound I is in substantially pure form. A suitable amount of Compound I in the oral dosage form is, for example, in the range of from about 1 to 500 mg.

The present invention further provides a method for treating a proliferative disease, comprising administering to a mammalian species in need thereof, a therapeutically effective amount of Compound I, wherein Compound I is provided in a crystalline form comprising Form N-1. Preferably, Compound I consists essentially of Form N-1. Preferably, the mammalian species is human.

USE AND UTILITY

Compound I is useful for inhibiting protein kinases, such as, for example, VEGF. More specifically, Compound I inhibits the effects of VEGF, a property of value in the treatment of disease states associated with angiogenesis and/or increased vascular permeability such as cancer. The present invention also relates to a pharmaceutical composition comprising Compound I, wherein Compound I is in crystalline Form N-1, and a pharmaceutically acceptable carrier or diluent; and to the use of this pharmaceutical composition in the treatment of hyperproliferative disorder in mammal. In particular, the pharmaceutical composition may be employed to inhibit the growth of those primary and recurrent solid tumors which are associated with VEGF, especially those tumors which are significantly dependent on VEGF for their growth and spread, including for example, cancers of the bladder, squamous cell, head, colorectal, oesophageal, gynecological (such as ovarian), pancreas, breast, prostate, lung, vulva, skin, brain, genitourinary tract, non-small cell lung cancer (NSCLC), lymphatic system (such as thyroid), stomach, larynx, and lung. In another embodiment, Compound I is also useful in the treatment of noncancerous disorders such as diabetes, diabetic retinopathy, psoriasis, rheumatoid arthritis, obesity, Kaposi's sarcoma, haemangioma, acute and chronic nephropathies (including proliferative glomerulonephritis and diabetes-induced renal disease), atheroma, arterial restenosis, autoimmune diseases, acute inflammation and ocular diseases with retinal vessel proliferation, diabetic retinopathy, retinopathy of prematurity and macular degeneration. Compound I may be employed in the prevention of blastocyte implantation in a mammal, or in the treatment of atherosclerosis, eczema, scleroderma, or hemangioma. Compound I possesses good activity against VEGF receptor tyrosine kinase while possessing some activity against other tyrosine kinases.

Thus according to a further aspect of the invention, there is provided the use of Compound I, wherein Compound I is in Form N-1, in the manufacture of a medicament for use in the production of an antiangiogenic and/or vascular permeability reducing effect in a mammalian animal such as a human being.

According to a further feature of the invention there is provided a method for producing an antiangiogenic and/or vascular permeability reducing effect in a mammalian animal, such as a human being, in need of such treatment which comprises administering to said animal an effective amount of Form N-1 of Compound I as defined herein before.

Compound I may also inhibit other receptor tyrosine kinases including HER1 and HER2 and is therefore useful in the treatment of proliferative disorders such as psoriasis and cancer. The HER1 receptor kinase has been shown to be expressed and activated in many solid tumors including non-small cell lung, colorectal, and breast cancer. Similarly, the HER2 receptor kinase has been shown to be overexpressed in breast, ovarian, lung, and gastric cancer. Monoclonal antibodies that downregulate the abundance of the HER2 receptor or inhibit signaling by the HER1 receptor have shown anti-tumor efficacy in preclinical and clinical studies. It is therefore expected that inhibitors of the HER1 and/or HER2 kinases will have efficacy in the treatment of tumors that depend on signaling from either of the two receptors. The ability of Compound I to inhibit HER1 further adds to their use as anti-angiogenic agents. See the following documents and references cited therein: Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), pp. 2639-2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), pp. 904-914 (2000).

The antiproliferative, antiangiogenic, and/or vascular permeability reducing treatment defined herein before may be applied as a sole therapy or may involve, in addition to Compound I, one or more other substances and/or treatments. Such conjoint treatment may be achieved by way of the simultaneous, sequential, or separate administration of the individual components of the treatment. Compound I may also be useful in combination with known anti-cancer and cytotoxic agents and treatments, including radiation. If formulated as a fixed dose, such combination products employ Compound I within the dosage range described below and the other pharmaceutically active agent within its approved dosage range. Compound I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology, the other component(s) of such conjoint treatment in addition to the antiproliferative, antiangiogenic, and/or vascular permeability reducing treatment defined herein before may be: surgery, radiotherapy, or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, and razoxane);

(ii) cytostatic agents such as antiestrogens (for example tamoxifen, toremifene, raloxifene, droloxifene, and iodoxifene), progestogens (for example megestrol acetate), aromatase inhibitors (for example anastrozole, letrozole, borazole, and exemestane), antihormones, antiprogestogens, antiandrogens (for example flutamide, nilutamide, bicalutamide, and cyproterone acetate), LHRH agonists and antagonists (for example gosereline acetate and leuprolide), inhibitors of testosterone 5α-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such as growth factor antibodies, growth factor receptor antibodies such as Avastin® (bevacizumab) and Erbitux® (cetuximab); tyrosine kinase inhibitors, and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); intercalating antitumor antibiotics (for example anthracyclines like doxorubicin, daunomycin, epirubicin, idarubicin, mitomycin-C, dactinomycin, and mithramycin); platinum derivatives (for example cisplatin and carboplatin); alkylating agents (for example nitrogen mustard, melphalan, chlorambucil, busulphan, cyclophosphamide, ifosfamide nitrosoureas, thiotepa; anti-mitotic agents (for example vinca alkaloids like vincristine and taxoids like Taxol® (paclitaxel), Taxotere® (docetaxel) and newer microbtubule agents such as epothilone analogs, discodermolide analogs, and eleutherobin analogs); topoisomerase inhibitors (for example epipodophyllotoxins like etoposide, teniposide, amsacrine, and topotecan); cell cycle inhibitors (for example flavopyridols); biological response modifiers, and proteasome inhibitors such as Velcade® (bortezomib).

As stated above, Compound I is of interest for its antiangiogenic and/or vascular permeability reducing effects. This compound is expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, Compound I is useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burkett's lymphoma;

hematopoietic tumors of myeloid lineage, including acute and chronic myelogenous leukemias, myelodysplastic syndrome, and promyelocytic leukemia;

tumors of mesenchymal origin, including fibrosarcoma and rhabdomyosarcoma;

tumors of the central and peripheral nervous system, including astrocytoma, neuroblastoma, glioma, and schwannomas; and other tumors, including melanoma, seminoma, teratocarcinoma, osteosarcoma, xeroderma pigmentosum, keratoacanthoma, thyroid follicular cancer, and Kaposi's sarcoma.

Due to the key role of kinases in the regulation of cellular proliferation in general, inhibitors can act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compound I may induce or inhibit apoptosis. The apoptotic response is aberrant in a variety of human diseases. Compound I, as a modulator of apoptosis, would be useful in the treatment of cancer (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases, and cancer pain.

Compound I is especially useful in treatment of tumors having a high incidence of tyrosine kinase activity, such as colon, lung, and pancreatic tumors. By the administration of a composition (or a combination) comprising Compound I, development of tumors in a mammalian host is reduced.

Compound I may also be useful in the treatment of diseases other than cancer that may be associated with signal transduction pathways operating through growth factor receptors such as VEGFR-2 and FGFR-1.

Compound I in Form N-1 may be formulated with a pharmaceutical vehicle or diluent for oral, intravenous, or subcutaneous administration. The pharmaceutical composition can be formulated in a classical manner using solid or liquid vehicles, diluents, and/or additives appropriate to the desired mode of administration. Orally, Form N-1 of Compound I can be administered in the form of tablets, capsules, granules, powders, and the like. Crystalline Form N-1 of Compound I may also be administered as a suspension using carriers appropriate to this mode of administration.

The effective amount of Compound I may be determined by one of ordinary skill in the art, and includes exemplary dosage amounts for a mammal of from about 0.05 to about 300 mg/kg/day, preferably less than about 200 mg/kg/day, in a single dose or in 2 to 4 divided doses. It will be understood that the specific dose level and frequency of dosage for any particular subject may be varied and will depend upon a variety of factors, the bioavailability of Compound I in Form N-1, the metabolic stability and length of action of Compound I, the species, age, body weight, general health, sex, and diet of the subject, the mode and time of administration, rate of excretion, drug combination, and severity of the particular condition. Preferred subjects for treatment include animals, most preferably mammalian species such as humans and domestic animals such as dogs, cats, horses, and the like.

Exemplary compositions for oral administration include suspensions comprising particles of Compound I in Form N-1 dispersed in a liquid medium. The suspension may further comprise, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate, and/or lactose and/or other excipients, binders, extenders, disintegrants, diluents, and lubricants such as those known in the art. Compound I in Form N-1 also may be delivered by sublingual and/or buccal administration, e.g. with molded, compressed, or freeze-dried tablets. Exemplary compositions may include fast-dissolving diluents such as mannitol, lactose, sucrose, and/or cyclodextrins. Also, included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (CARBOPOL 934®). Lubricants, glidants, flavors, coloring agents, and stabilizers may also be added for ease of fabrication and use.

An example of a composition for oral administration is Compound I in crystalline Form N-1, lactose monohydrate (intra-granular phase), microcrystalline cellulose (intra-granular phase), croscarmellose sodium (intra-granular phase), hydroxypropyl cellulose (intra-granular phase), microcrystalline cellulose (extra-granular phase), croscarmellose sodium (extra-granular phase), and magnesium stearate (extragranular phase).

Typically, the solid form of a pharmaceutically active material is important in the preparation of a solid dosage form, such as tablets or capsules as the manufacturing, stability, and/or the performance of the pharmaceutically active material can be dependent upon the solid form. Generally, a crystalline form provides pharmaceutically active material with uniform properties, such as solubility, density, dissolution rate, and stability. In the present invention, Compound I in the crystalline form N-1 has properties suitable for the manufacture of tablets or capsules, for providing a stable oral dosage form, and/or for delivery of Compound I to a patient in need thereof.

Methods of Preparation and Characterization

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, 2*nd* Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, pp. 369-377. In general, seeds of small size are needed to control effectively the growth of crystals in the batch. Seed of small size may be generated by sieving, milling, or micronizing of large crystals, or by microcrystallization of solutions. Care should be taken that milling or micronizing of crystals does not result in any change in crystallinity from the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, powder x-ray diffraction, or the like, to assure formation of the preferred crystalline form of the product. The resulting crystalline form may be produced in an amount of greater than about 70 weight % isolated yield, preferably greater than 90 weight % isolated yield, based on the weight of the compound originally employed in the crystallization procedure. The product may be comilled or passed through a mesh screen to delump the product, if necessary.

Crystalline forms may be prepared directly from the reaction medium of the final process for preparing Compound I. This may be achieved, for example, by employing in the final process step a solvent or a mixture of solvents from which Compound I may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

The presence of more than one crystalline form and/or polymorph in a sample may be determined by techniques such as powder x-ray diffraction (PXRD) or solid state nuclear magnetic resonance spectroscopy. For example, the presence of extra peaks in the comparison of an experimentally measured PXRD pattern with a simulated PXRD pattern may indicate more than one crystalline form and/or polymorph in the sample. The simulated PXRD may be calculated from single crystal x-ray data. see Smith, D. K., "*A FORTRAN Program for Calculating X-Ray Powder Diffraction Patterns*," Lawrence Radiation Laboratory, Livermore, Calif., UCRL-7196 (April 1963).

Form N-1 of Compound I according to the invention may be characterized using various techniques, the operation of which are well known to those of ordinary skill in the art. Form N-1 of Compound I may be characterized and distinguished using single crystal x-ray diffraction performed under standardized operating conditions and temperatures, which is based on unit cell measurements of a single crystal of the form at a fixed analytical temperature. The approximate unit cell dimensions in Angstroms (Å), as well as the crystalline cell volume, spatial grouping, molecules per cell, and crystal density may be measured, for example at a sample temperature of 25° C. A detailed description of unit cells is provided in Stout & Jensen, X-Ray Structure Determination: A Practical Guide, Macmillan Co., New York (1968), Chapter 3, which is herein incorporated by reference.

Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, both run at the same analytical temperature, and measurements for the subject form characterized as a series of 2θ values (usually four or more).

Other means of characterizing the form may be used, such as solid state nuclear magnetic resonance (NMR), differential scanning calorimetry, thermography, and gross examination of the crystalline or amorphous morphology. These parameters may also be used in combination to characterize the subject form.

The crystalline form was analyzed using one or more of the testing methods described below.

Single Crystal X-Ray Measurements

Single crystal x-ray data for Example 1 was collected. For this analysis, a Bruker-Nonius CAD4 serial diffractometer (Bruker Axs, Inc., Madison Wis.); or alternately, a Bruker-Nonius Kappa CCD 2000 system using Cu Kα radiation ($\lambda$=1.5418 Å) was used. Unit cell parameters were obtained through least-squares analysis of the experimental diffractometer settings of 25 high-angle reflections. Intensities were measured using Cu Kα radiation ($\lambda$=1.5418 Å) at a constant temperature with the θ-2θ variable scan technique and were corrected only for Lorentz-polarization factors. Background counts were collected at the extremes of the scan for half of the time of the scan. Indexing and processing of the measured intensity data were carried out with the HKL2000 software package in the Collect program suite R. Hooft, Nonius B. V. (1998). When indicated, crystals were cooled in the cold stream of an Oxford cryogenic system during data collection.

The structures were solved by direct methods and refined on the basis of observed reflections using either the SDP software package SDP, Structure Determination Package, Enraf-Nonius, Bohemia, N.Y.) with minor local modifications or the crystallographic package, MAXUS (maXus solution and refinement software suit: S. Mackay, C. J. Gilmore, C. Edwards, M. Tremayne, N. Stewart, and K. Shankland. maXus is a computer program for the solution and refinement of crystal structures from diffraction data.

Powder X-Ray Diffraction

Powder x-ray diffraction (PXRD) data were obtained using a Bruker GADDS (General Area Detector Diffraction System) manual chi platform goniometer. Powder samples were placed in thin walled glass capillaries of 1 mm or less in diameter; the capillary was rotated during data collection. The sample-detector distance was 17 cm. The radiation was Cu Kα ($\lambda$=1.5418 Å). Data were collected for 3<2θ<35° with a sample exposure time of at least 300 seconds.

The derived atomic parameters (coordinates and temperature factors) were refined through full matrix least-squares. The function minimized in the refinements was $\Sigma_w(|F_O|-|F_C|)^2$. R is defined as $\Sigma||F|-|F||/\Sigma|F_O|$ while $R_w=[\Sigma_w(|F_O|-|F_C|)^2/\Sigma_w|F_O|^2]^{1/2}$ where w is an appropriate weighting function based on errors in the observed intensities. Difference maps were examined at all stages of refinement. Hydrogen atoms were introduced in idealized positions with isotropic temperature factors, but no hydrogen parameters were varied.

Melting Points

A melting point for Form N-1 of Compound 1 was determined by hot stage microscopy. Crystals were placed on a glass slide, covered with a cover slip, and heated on a Linkham LTS350 hot stage mounted on a microscope (Linkham Scientific Instruments Ltd, Tadworth, U.K.). The heating rate was controlled at 10° C./min for the temperature range, ambient to 300° C. The crystals were observed visually for evidence of phase transformation, changes in birefringence, opacity, melting, and/or decomposition.

Differential Scanning Calorimetry

Differential scanning calorimetry (DSC) was conducted for each crystalline form using a TA Instruments™ model Q1000. For each analysis, the DSC cell/sample chamber was purged with 100 ml/min of ultra-high purity nitrogen gas. The instrument was calibrated with high purity indium. The heating rate was 10° C. per minute in the temperature range between 25 and 300° C. The heat flow, which was normalized by sample weight, was plotted versus the measured sample temperature. The data were reported in units of watts/gram ("W/g"). The plot was made with the endothermic peaks pointing down. The endothermic melt peak (melting point) was evaluated for extrapolated onset temperature.

EXAMPLES

Example 1

Preparation of Form N-1 of Compound I

To 100-mL round bottom flask was added 8.6 g Compound I, 60 mL N,N-dimethyl formamide, and 4.94 g ammonium formate. The mixture was placed under a nitrogen atmosphere, and then 636 mg 5% Pd/C catalyst was added. After 4 hours and 20 minutes at 45° C., the extent of reaction was measured to be approximately 50% as measured by thin layer chromatography. An additional charge of 200 mg catalyst and 1 g ammonium formate was added, and the contents of the flask were allowed to react for an additional four hours at 45° C. The reaction mixture was filtered through Celite and chased with 50 mL ethyl acetate three times. The combined filtrate was washed with 150 mL water, and the resulting aqueous phase was back-extracted with an additional 50 mL ethyl acetate. The aqueous phase was basified with aqueous ammonia, then back extracted again with 50 mL ethyl acetate. The organic solutions were combined and washed with 100 mL water three times, 100 mL brine once, and then dried over magnesium sulfate. Solvent was removed via vacuum distillation to give 6.5 g residue. The residue was then purified by column chromatography using silica gel 60, ethyl acetate: isopropyl alcohol:triethyl amine (88:10:2). Purified fractions were combined, stripped of solvent, and rechromatographed to give 4.1 g residue. Trituration of the amorphous residue with toluene produced a white, solid precipitate. The crystalline solid was filtered, washed with toluene, and dried in a vacuum oven at ambient temperature for three days. Yield was 2.3 g of Compound I as a crystalline solid, with an HPLC purity of 99%. Elemental analysis gave; C, 59.81% (59.85); H, 5.30% (5.48); N, 15.72% (15.86); F, 4.52 (4.30); where the numbers in parentheses are theoretical. Single crystal x-ray analysis and powder x-ray diffraction were then used for further characterization, and the crystal form was given the designation N-1.

Example 2

Preparation of Form N-1 of Compound I

One kilogram of Compound I was added as a solid to a 20 L reactor, followed by the addition of 4 L of ethyl acetate. The resulting slurry was heated to 50° C. until a clear solution was obtained. Next, 4 L of n-heptane was added through a dropping funnel over a period of approximately 30 minutes. Then, approximately 10 g (1% by wt.) of N1 seeds of Compound I were added to the reactor. Solid was observed to start crystallizing from the batch. The contents of the reactor were maintained at a temperature of 50° C. for 30 minutes, and then allowed to cool to 40° C. Next, an additional 4 L of heptane was added over 30 minutes. The contents of the reactor were maintained at 40° C. for another 30 minutes, and then allowed to cool to 20° C. over 1 hour. The resulting slurry was filtered (by Buchner funnel and filter paper), washed with 5 L of ethyl acetate/heptane (1:4 mixture) followed by 3 L of heptane, and dried at 40-50° C. in a vacuum oven until a constant weight was obtained. The yield was in the range of 85-90%.

Example 3

Preparation of Tablets Comprising Form I of Compound I

The granulation for tablets was prepared by combining with mixing the intragranular materials Compound I, microcrystalline cellulose NF (PH 102), and crospovidone in a high shear mixer granulator for 15 minutes. Then intragranular magnesium stearate was added to the blend and mixed an additional 5 minutes in the high shear mixer granulator. The resulting powder was granulated or densified with a slugging process and yielded slugs with a weight in the range of 0.9 to 1.1 grams and a hardness in the range of 7 SCU to 13 SCU (Strong Cobb Units). The slugs were then screened through a #18 mesh screen. The second portion of crospovidone (extragranular) was added to the screened granules in a tumble blender and mixed for 15 minutes. Magnesium stearate (extragranular) was then added to the blend in a tumble blender and mixed for 5 minutes to give the final blend. The final blend was compressed on a tablet press into 60-mg strength tablets (240 mg tablet weight) and 200-mg strength tablets (800 mg tablet weight) to a target hardness of 18 SCU (Strong Cobb Units).

TABLE 2

| Material | Amount (wt. %) |
|---|---|
| Intragranular: | |
| Microcrystalline Cellulose NF (PH 102) | 68.00 |
| Compound I | 25.00 |
| Crospovidone | 3.00 |
| Magnesium Stearate | 0.50 |
| Extragranular: | |
| Crospovidone | 3.00 |
| Magnesium Stearate | 0.50 |

What is claimed is:

1. Compound I:

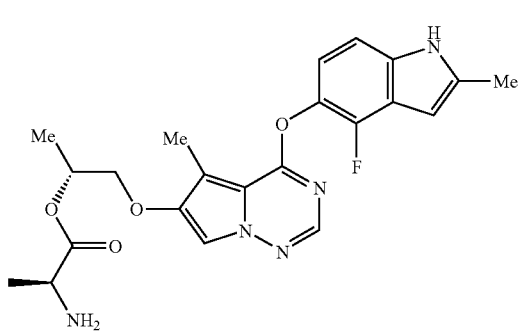

(I)

in crystalline form N-1.

2. The crystalline form according to claim 1 characterized by unit cell parameters equal to the following:
Cell dimensions: a=9.85 Å
   b=8.06 Å
   c=14.98 Å
   α=90.0°
   β=106.9°
   γ=90.0°
Space group: $P2_1$
Molecules/unit cell: 2
wherein measurement of said crystalline form is at a temperature of about 25° C.

3. The crystalline form according to claim 1 characterized by fractional atomic coordinates as listed below

TABLE 1

Positional Parameters and Isotropic Temperature Factors for Form N-1 of Compound I

| Atom | X | Y | V | B(iso) |
|---|---|---|---|---|
| N1 | 0.1753(6) | 0.332(6) | 0.1945(4) | 4.5(1) |
| F2 | 0.7015(6) | 0.490(6) | 0.2322(4) | 7.4(1) |
| N3 | 0.4379(7) | 0.291(5) | 0.3144(5) | 5.7(1) |
| C4 | 0.2652(8) | 0.468(6) | 0.2142(5) | 5.1(1) |
| O5 | −0.2575(7) | 0.807(6) | 0.1106(5) | 6.6(1) |
| C6 | 0.3977(8) | 0.436(6) | 0.2779(6) | 4.9(1) |
| C7 | 0.8707(9) | 0.549(6) | 0.3780(6) | 5.4(2) |
| C8 | 0.0601(9) | 0.543(6) | 0.1156(6) | 5.2(2) |
| N9 | 0.2102(8) | 0.175(6) | 0.2301(5) | 6.0(1) |
| O10 | −0.0356(8) | 0.651(6) | 0.0632(5) | 7.1(2) |
| C11 | 0.0471(8) | 0.377(6) | 0.1340(6) | 5.2(1) |
| N12 | 1.0349(8) | 0.609(6) | 0.5111(6) | 6.2(2) |

TABLE 1-continued

Positional Parameters and Isotropic Temperature Factors for Form N-1 of Compound I

| Atom | X | Y | V | B(iso) |
|---|---|---|---|---|
| C13 | −0.2106(8) | 0.957(5) | 0.1410(5) | 4.8(1) |
| C14 | −0.2689(9) | 0.752(6) | 0.0168(6) | 5.7(2) |
| C15 | 0.896(1) | 0.593(6) | 0.4733(6) | 5.7(2) |
| O16 | 0.4805(8) | 0.571(6) | 0.2994(5) | 7.2(2) |
| C17 | 1.103(1) | 0.582(6) | 0.4457(6) | 5.9(2) |
| C18 | 0.337(1) | 0.170(6) | 0.2876(7) | 6.0(2) |
| C19 | 1.006(1) | 0.548(6) | 0.3630(6) | 5.9(2) |
| C20 | −0.1928(9) | 0.978(6) | 0.2425(6) | 5.4(1) |
| C21 | 0.192(1) | 0.6030(6) | 0.1648(6) | 6.0(2) |
| C22 | 0.7301(9) | 0.530(6) | 0.3229(6) | 5.7(2) |
| O23 | −0.1971(9) | 1.067(6) | 0.0900(6) | 7.9(2) |
| N24 | −0.1133(9) | 1.130(5) | 0.2815(6) | 6.9(2) |
| C25 | 0.622(1) | 0.561(6) | 0.3608(7) | 6.5(2) |
| C26 | 0.647(1) | 0.600(6) | 0.4545(8) | 7.0(2) |
| C27 | −0.1781(9) | 0.602(5) | 0.0279(6) | 6.0(2) |
| C28 | 0.781(1) | 0.613(6) | 0.5101(7) | 6.9(2) |
| C29 | −0.332(1) | 0.969(5) | 0.2614(8) | 7.3(2) |
| C30 | 1.261(1) | 0.608(5) | 0.4672(9) | 7.6(2) |
| C31 | −0.426(1) | 0.723(6) | −0.0321(1) | 9.7(3) |
| C32 | 0.246(1) | 0.775(6) | 0.166(1) | 9.1(3) |
| H33 | −0.0444 | 0.2942 | 0.1053 | 5.9159 |
| H34 | 1.0869 | 0.6372 | 0.5838 | 7.2815 |
| H35 | −0.2278 | 0.8448 | −0.0201 | 7.092 |
| H36 | 0.371 | 0.0448 | 0.3177 | 6.7846 |
| H37 | 1.0278 | 0.5242 | 0.2971 | 6.9187 |
| H38 | −0.1326 | 0.8694 | 0.2792 | 6.2069 |
| H39 | 0.564 | 0.6129 | 0.4838 | 8.6991 |
| H40 | −0.2086 | 0.5118 | 0.0747 | 7.0122 |
| H41 | −0.1973 | 0.5371 | −0.0399 | 7.0122 |
| H42 | 0.8024 | 0.6379 | 0.584 | 8.3185 |
| H43 | 1.2929 | 0.5738 | 0.4072 | 9.183 |
| H44 | 1.3124 | 0.5163 | 0.5239 | 9.183 |
| H45 | 1.2882 | 0.7267 | 0.4905 | 9.183 |
| H46 | −0.4376 | 0.6764 | −0.1023 | 11.2165 |
| H47 | −0.4852 | 0.8276 | −0.0316 | 11.2165 |
| H48 | −0.4611 | 0.6193 | 0.0059 | 11.2165 |
| H49 | 0.1629 | 0.8462 | 0.1181 | 12.1131 |
| H50 | 0.3367 | 0.7700 | 0.1367 | 12.1131 |
| H51 | 0.2760 | 0.8228 | 0.2327 | 12.1131 |
| H52 | −0.3172 | 0.9408 | 0.3368 | 8.4573 |
| H53 | −0.3957 | 0.8650 | 0.223 | 8.4573 |
| H54 | −0.396 | 1.0803 | 0.2447 | 8.4573 |
| H55 | −0.1754 | 1.2337 | 0.2473 | 8.0256 |
| H56 | −0.0126 | 1.1268 | 0.2706 | 8.0256. |

4. The crystalline form according to claim 1 characterized by a powder x-ray diffraction pattern comprising four or more 2θ values (CuKα λ=1.5418 Å) selected from the group consisting of 9.4±0.2, 12.6±0.2, 13.2±0.2, 14.5±0.2, 16.6±0.2, 17.2±0.2, 18.2±0.2, 18.8±0.2, 21.3±0.2, 21.6±0.2, and 22.1±0.2, wherein measurement of said crystalline form is at a temperature of about 25° C.

5. The crystalline form according to claim 1 characterized by a powder x-ray diffraction pattern comprising five or more 2θ values (CuKα λ=1.5418 Å) selected from the group consisting of 9.4±0.2, 12.6±0.2, 13.2±0.2, 14.5±0.2, 16.6±0.2, 17.2±0.2, 18.2±0.2, 18.8±0.2, 21.3±0.2, 21.6±0.2, and 22.1±0.2, wherein measurement of said crystalline form is at a temperature of about 25° C.

6. The crystalline form according to claim 1 characterized by one or more of the following:
a) unit cell parameters substantially equal to the following:
Cell dimensions: a=9.85 Å
   b=8.06 Å
   c=14.98 Å
   α=90.0°
   β=106.9°
   γ=90.0°

Space group: P2$_1$
Molecules/unit cell: 2
wherein measurement of said crystalline form is at a temperature of about 25° C.;
b) a powder x-ray diffraction pattern comprising five or more 2θ values (CuKαλ=1.5418 Å) selected from the group consisting of 9.4±0.2, 12.6±0.2, 13.2±0.2, 14.5±0.2, 16.6±0.2, 17.2±0.2, 18.2±0.2, 18.8±0.2, 21.3±0.2, 21.6±0.2, and 22.1±0.2, wherein measurement of said crystalline form is at a temperature of about 25° C.; and/or
c) a melting point in the range of from about 138° C. to about 144° C.

* * * * *

UNITED STATES PATENT AND TRADEMARK OFFICE
CERTIFICATE OF CORRECTION

| | | |
|---|---|---|
| PATENT NO. | : 7,932,383 B2 | Page 1 of 1 |
| APPLICATION NO. | : 12/480177 | |
| DATED | : April 26, 2011 | |
| INVENTOR(S) | : John Thornton | |

It is certified that error appears in the above-identified patent and that said Letters Patent is hereby corrected as shown below:

On the title page, In Column 2, Line 13:
Delete "R.D. ," and insert -- R.D., --

In Column 16, Line 46:
In Claim 4, delete "2θvalues" and insert -- 2θ values --

In Column 17, Line 6:
In Claim 6, delete "2θvalues" and insert -- 2θ values --

In Column 17, Line 6:
In Claim 6, delete "(CuKαλ" and insert -- (CuKα λ --

Signed and Sealed this
Fourth Day of October, 2011

David J. Kappos
*Director of the United States Patent and Trademark Office*